United States Patent [19]

Kellar et al.

[11] Patent Number: 5,401,492
[45] Date of Patent: Mar. 28, 1995

[54] WATER INSOLUBLE NON-MAGNETIC MANGANESE PARTICLES AS MAGNETIC RESONANCE CONTRAST ENHACEMENT AGENTS

[75] Inventors: Kenneth E. Kellar, Malvern, Pa.; Piotr H. Karpinski, Fairport, N.Y.; Elaine Liversidge, West Chester, Pa.; Wolfgang H. H. Gunther, West Chester, Pa.; Gregory L. McIntire, West Chester, Pa.; Barbara Van Orman, West Chester, Pa.

[73] Assignee: Sterling Winthrop, Inc., New York, N.Y.

[21] Appl. No.: 991,893

[22] Filed: Dec. 17, 1992

[51] Int. Cl.$^6$ .................. A61B 5/055; A61K 33/42; A61K 33/32
[52] U.S. Cl. ........................ 424/9; 424/604; 424/639; 514/836; 436/173; 128/653.4; 128/654
[58] Field of Search .................. 424/9, 604, 639; 514/836; 436/173; 128/653.4, 654

[56] References Cited

U.S. PATENT DOCUMENTS

| | | | |
|---|---|---|---|
| 4,346,709 | 8/1982 | Schmitt | 128/260 |
| 4,720,386 | 1/1988 | McCollester | 424/88 |
| 4,735,796 | 4/1988 | Gordon | 424/9 |
| 4,889,931 | 12/1989 | Rocklage et al. | 540/465 |
| 4,916,246 | 4/1990 | Felder et al. | 556/1 |
| 4,960,589 | 10/1990 | Sasagawa | 424/442 |
| 5,077,037 | 12/1991 | Wallace | 424/9 |
| 5,143,716 | 9/1991 | Inger | 424/9 |

*Primary Examiner*—Gary E. Hollinden
*Attorney, Agent, or Firm*—William J. Davis

[57] ABSTRACT

This invention is directed to a magnetic resonance imaging composition for imaging of an organ rich in mitochondria comprising particles of a substantially insoluble manganese compound. In a preferred embodiment, the organ rich in mitochondria is the liver. In a further preferred embodiment, the particles are substantially nonmagnetic. In another preferred embodiment, the particles have a particle size of less than about 10 microns.

In a still further preferred embodiment, the insoluble manganese compound is a manganese salt. The manganese compound is preferably selected from the group consisting of manganese phosphate, manganese carbonate and manganese 8-hydroxy quinolate.

In another preferred embodiment, the composition of the present invention further comprises a surfactant.

The present invention is also directed to a method of diagnosis comprising administering to a mammal a contrast effective amount of particles of a substantially insoluble manganese compound suspended or dispersed in a physiologically tolerable carrier and generating an NMR image of said mammal.

7 Claims, 3 Drawing Sheets

WATER INSOLUBLE NON-MAGNETIC MANGANESE PARTICLES AS MAGNETIC RESONANCE CONTRAST ENHACEMENT AGENTS

FIELD OF THE INVENTION

This invention relates to diagnostic compositions useful in magnetic resonance imaging. More particularly, this invention relates to water insoluble manganese particles that can be used in magnetic resonance imaging of organs.

BACKGROUND OF THE INVENTION

The enhancement of positive contrast in the magnetic resonance (MR) image of an organ rich in mitochondria, such as the liver, pancreas, or kidney, requires an agent that specifically locates in those organs and causes an increase in the longitudinal relaxation rate of water protons in those organs. The increase in the relaxation rate, which is responsible for enhancing positive contrast, is due to a dipolar interaction between the magnetic moments of the water protons and the magnetic moments of the paramagnetic contrast enhancement agent. The increase in the relaxation rate per unit concentration of paramagnetic contrast enhancement agent is called the relaxation efficiency, or relaxivity, of the agent.

Runge et al., U.S. Pat. No. 4,615,879 discloses a contrast media composition for nuclear magnetic resonance (NMR) imaging of the gastrointestinal tract. The compositions prepared in that invention provided a decrease in both the spin lattice ($T_1$) and the spin-spin ($T_2$) relaxation time of protons, thereby increasing the imaging of the gastrointestinal tract.

However, it would be desirable to have a composition for MR imaging which, in its native form, did not affect proton $T_1$ and $T_2$, that is, a composition which is substantially nonmagnetic, and which becomes a contrast agent upon in vivo administration. The present invention provides for a MR imaging composition for MR imaging of organs such as the liver.

BRIEF DESCRIPTION OF THE INVENTION

This invention is directed to a magnetic resonance imaging composition for imaging of an organ rich in mitochondria comprising particles of a substantially insoluble manganese compound. In a preferred embodiment, the organ rich in mitochondria is the liver. In a further preferred embodiment, the particles are substantially nonmagnetic. In another preferred embodiment, the particles have a particle size of less than about 10 microns.

In a still further preferred embodiment, the insoluble manganese compound is a manganese salt. The manganese compound is preferably selected from the group consisting of manganese phosphate, manganese carbonate and manganese 8-hydroxy quinolate.

In another preferred embodiment, the composition of the present invention further comprises a surfactant.

The present invention is further directed to a method of preparing a magnetic resonance imaging composition useful for imaging an organ rich in mitochondria comprising particles of a substantially insoluble manganese compound comprised of contacting a manganese source, preferably a manganese (II) source, with a counter ion source for a time and under conditions sufficient for the formation of said insoluble manganese compound. In a preferred embodiment, the contacting is by simultaneous admixing in an aqueous solution.

In a further preferred embodiment, the manganese source is an aqueous solution of a soluble manganese salt. The soluble manganese salt is preferably selected from the group consisting of manganese chloride, manganese nitrate and manganese sulfate.

In a still further preferred embodiment, the counter ion source is an aqueous solution of a carbonate salt. The carbonate salt is preferably selected from the group consisting of sodium carbonate, potassium carbonate, and ammonium carbonate.

In another preferred embodiment, the counter ion source is an aqueous solution of a phosphate salt. The phosphate salt is preferably selected from the group consisting of sodium phosphate, potassium phosphate, and ammonium phosphate.

In yet another preferred embodiment, the counter ion source is an aqueous solution of 8-quinolinol.

The present invention is also directed to a method of diagnosis comprising administering to a mammal a contrast effective amount of particles of a substantially insoluble manganese compound suspended or dispersed in a physiologically tolerable carrier and generating an NMR image of said mammal.

DETAILED DESCRIPTION OF THE INVENTION

Figure 1:
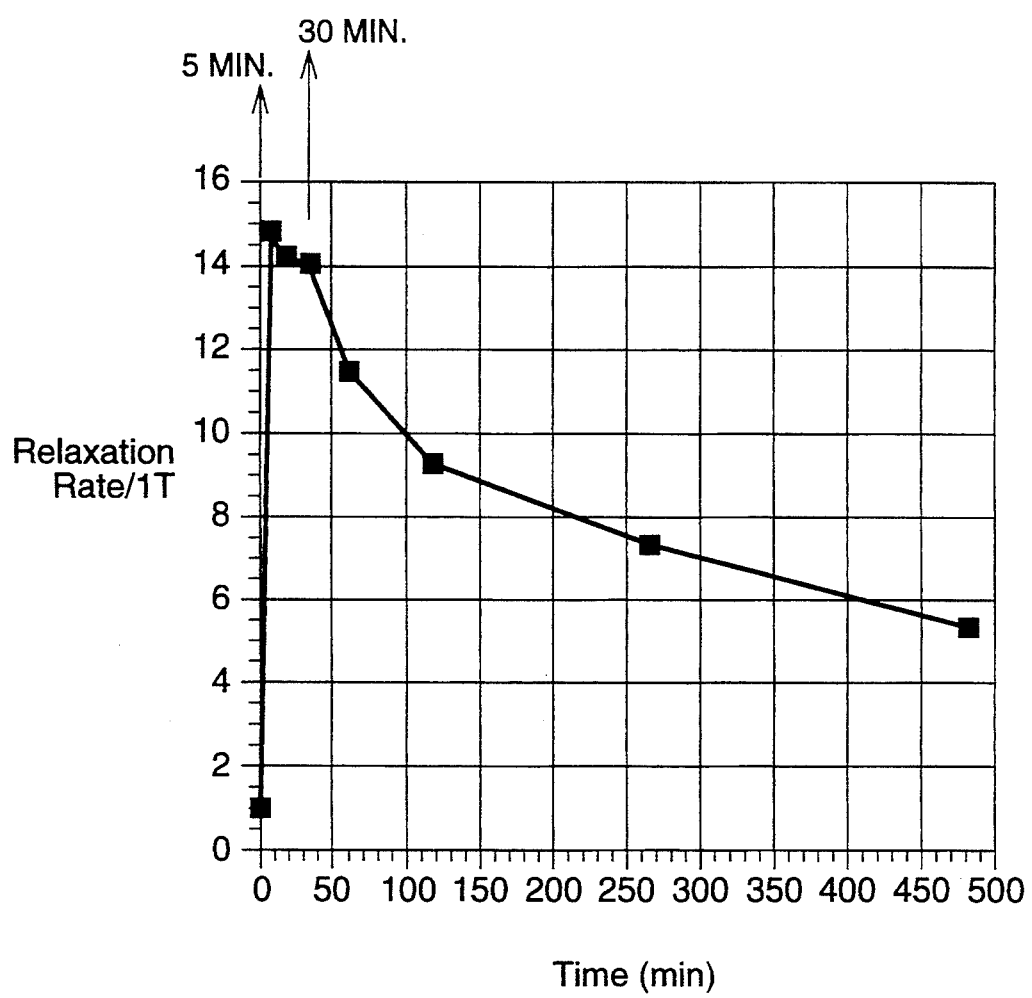
FIG. 1 shows the change in relaxivity of the tissue with time after injection of the insoluble manganese particles of the present invention.

This invention is described hereinafter in connection with a preferred embodiment featuring particles of a substantially insoluble manganese compound. In addition, it is believed that the invention can be practiced with particles of other substantially insoluble compounds.

The relaxivity of the contrast enhancement agent in organs such as the liver is not necessarily the same as the relaxivity of the agent in a beaker of water. Although the relaxivities of various manganese-containing agents are different in water, these agents have the same relaxivity in liver homogenates.

Although not wishing to be bound by theory, this similarity of relaxivities in liver homogenates suggests that manganese-containing agents are merely vehicles that deliver manganese to the liver, where the manganese is stripped from the agent and becomes bound to some macromolecule in the liver. It is the relaxivity of the manganese-liver macromolecule complex that is related to the enhancement of positive contrast in a liver MR image.

Although manganese is a targeting vector to organs such as the liver, not all of the injected dosage of manganese localizes in the liver. Manganese has been found in other organs as well.

One way of increasing liver specificity is to use water-insoluble manganese particles as contrast enhancement agents according to the composition of the present invention. Examples would include, but are not limited to, water-insoluble inorganic salts such as manganese phosphate or manganese carbonate, and manganese chelates. In general, water-insoluble particles with diameters ranging from about one hundred nanometers to a few micrometers are known to be taken up rapidly in the liver. Water-insoluble iron particles, which have a large $T_2$ (transverse relaxation time) effect on water protons under imaging conditions are currently being investigated as negative contrast enhancement agents for liver MR imaging. Unlike their iron counterparts, manganese particles do not significantly affect $T_1$ or $T_2$ of water protons. Any possible affect on $T_1$ or $T_2$ would be due to free manganese ions as a result of a solubility product. This effect can be removed by encapsulation of the manganeseparticles.

However, once localized in the liver, the manganese particle dissolves and releases manganese to form a manganese -liver macromolecule complex with a high relaxivity as explained in the previous paragraph. In summary, water-insoluble manganese particles afford higher liver specificity than water-soluble manganese chelates. As a result, the dosage of manganese required to enhance positive contrast in a liver MR image to a given extent will be less for water-insoluble manganese particles than for water-soluble manganese chelates.

The present invention is directed to a magnetic resonance imaging composition for imaging of organs rich in mitochondria comprising particles of a substantially insoluble manganese compound which, in its native form, is substantially nonmagnetic.

The residue of the particles is visualized by imaging that tissue with a magnetic resonance imaging system. The visualization of the residue of the particles can be accomplished with commercially available magnetic imaging systems such as a General Electric 1.5 T Signa imaging system [$^1$H resonant frequency 63.9 megahertz (Mhz)]. Commercially available magnetic resonance imaging systems are typically characterized by the magnetic field strength used, with a field strength of 2.0 Tesla as the current maximum and 0.2 Tesla as the current minimum.

For a given field strength, each detected nucleus has a characteristic frequency. For example, at a field strength of 1.0 Tesla, the resonance frequency for hydrogen is 42.57 Mhz; for phosphorus-31 it is 17.24 Mhz; and for sodium-23 it is 11.26 Mhz.

As used herein, the phrase "organs rich in mitochondria" refers to organ systems in the body of a mammal which contain an abundance of the organelle called mitochondria. One measure of mitochondrial abundance is the level of mitochondrial enzymes present in a particular organ system. Organs rich in mitochondria include the liver, kidney, pancreas and biliary network. Preferred organs rich in mitochondria include the liver and kidney. A more preferred organ rich in mitochondria is the liver.

In a preferred embodiment, the particles of the present invention, in their native form, are substantially nonmagnetic. That is, the particles have no effect on $T_1$ or $T_2$ as composed ex vivo. Once the particles are used in the diagnosis of a mammal, according to the methods of the present invention, the Mn within the particles is liberated to form a Mn bioconjugate, as discussed elsewhere herein.

In a further preferred embodiment, the particles of the present invention have a particle size of less than about 10 microns. As used herein, the phrase "particle size" refers to a number average particle size as measured by conventional particle size measuring techniques well known to those skilled in the art, such as sedimentation field flow fractionation, photon correlation spectroscopy, disk centrifugation, or scanning electron microscopy (SEM). The phrase "particle size of less than about 10 microns" as used herein means that at least 90 percent of the particles have a weight average particle size of less than about 10 microns when measured by the above-noted techniques. It is preferred that at least 95 percent, and, more preferably, at least 99 percent of the particles have a particle size of less than about 10 microns. A preferred particle size is less than about 5 microns. A more preferred particle size is less than about 2.5 microns.

In another preferred embodiment, the insoluble manganese compound of the present invention is a manganese salt. That is, the salt yields manganese ions when in solution. Preferred manganese salts include manganese oxide, manganese dioxide, manganese iodate, manganese oxalate, manganese hydroxide, manganese hydrogen phosphate, manganese sulfide, manganese phosphate, manganese carbonate, manganese bile salts such as manganese oleate, manganese stearate, manganese cholate, and manganese taurocholate, and manganese salts of various fatty acids, and the like. Particularly preferred manganese salts are manganese phosphate and manganese carbonate.

The insoluble manganese compound can be a manganese chelate such as manganese 8-hydroxy quinolate and manganese 2-methyl-8-hydroxyquinolate.

As used herein, the phrase "substantially insoluble manganese compound" refers to a manganese containing compound with a solubility product (Ksp) of less than about $1\times 10^{-6}$. Preferred substantially insoluble manganese compounds have a Ksp of less than about $5\times 10^{-7}$. Manganese compounds useful as a substantially insoluble manganese compound have Ksp values as follows: manganese iodate ($4.4\times 10^{-7}$), manganese oxalate ($1.7\times 10^{-7}$), manganese hydroxide ($2.1\times 10^{-13}$), manganese hydrogen phosphate ($1.4\times 10^{-13}$), manganese sulfide ($4.7\times 10^{-14}$), manganese 2-methyl-8-hydroxyquinolate ($4.5\times 10^{-19}$), manganese carbonate ($2.2\times 10^{-11}$), and manganese 8-hydroxy quinolate ($1.6\times 10^{-18}$). The solubility in plasma or in vivo may affect the preferred timing of imaging.

In another preferred embodiment, the composition of the present invention may contain a surfactant. Preferred surfactants include Pluronic F68 NF, which is a block copolymer of ethylene oxide and propylene oxide, dimyristoylphosphatidylglycerol (DMPG), Tetronic 908, Tween 20, Tween 80, Pluronic F-108, Tyloxapol, Henkel APG 325cs, polyvinyl alcohol, or PVP k-15. Preferred surfactants include DMPG and Pluronic F68 NF.

The present invention is further directed to a method of preparing a magnetic resonance imaging composition useful for imaging an organ rich in mitochondria comprising particles of a substantially insoluble manganese compound comprised of contacting a manganese source, preferably a manganese II source, with a counter ion source for a time and under conditions sufficient for the formation of said insoluble manganese compound. Such counter ions are typically anions which interact with the manganese cation to form an insoluble manganese compound.

As used herein, the phrase "a manganese source" refers to an aqueous solution which contains free manganese ions, that is, manganese ions available for chemical reaction. For example, an aqueous solution of manganese chloride would contain free manganese ions available for chemical reaction. The manganese ion source need not contain the counter ion, in this case, chloride, to be useful in the processes of the present invention.

A preferred manganese source is a soluble or insoluble manganese salt. Preferred soluble manganese salts include manganese chloride, manganese nitrate, manganese sulfate, manganese acetate, manganese fluoride, and the like. Other exemplary soluble manganese salts may be found in the Handbook of Chemistry and Physics, CRC Press, Cleveland, Ohio.

As used herein, the phrase "a counter ion source" refers to an aqueous solution which contains a free counter ion, that is, a counter ion which is available for chemical reaction. For example, an aqueous solution of sodium carbonate would contain free carbonate counter ions available for chemical reaction. The carbonate counter ion need not contain any other ions, in this case, sodium, to be useful in the processes of the present invention.

A preferred counter ion source is a soluble carbonate or phosphate salt. Preferred soluble carbonate salts include sodium carbonate, potassium carbonate, and ammonium carbonate. Preferred soluble phosphate salts include sodium phosphate, potassium phosphate, and ammonium phosphate. Other exemplary soluble carbonate and phosphate salts may be found in the Handbook of Chemistry and Physics, CRC Press, Cleveland, Ohio.

Another preferred counter ion source includes aqueous solutions of the salts of oleic and cholic acid.

A further preferred counter ion source is an aqueous solution of 8-quinolinol, which provides an 8-quinolinate counter ion in solution.

In a preferred embodiment, contacting of the manganese ion source and the counter ion source is by simultaneous admixing in an aqueous solution. This aqueous solution is sometimes referred to herein as the "host solution", that is, the solution into which the manganese ion source and counter ion source are simultaneously admixed.

The host solution may contain other buffers, salts, or surfactants useful in the processes of the present invention. For example, the host solution may contain citric acid, sodium citrate, ascorbic acid or other acids, bases or buffers to regulate the pH value of the host solution. Additionally, the host solution may contain a variety of surfactants and stabilizers, as is well known in the art. Several of theses surfactants and stabilizers have been discussed elsewhere herein.

In brief, using the processes of the present invention, suspensions of manganese particulates, are prepared by a double-jet precipitation technique, i.e., by an addition of two reagents, each at a predetermined flow rate, into a vessel containing an aqueous host solution. The host solution may, in addition to water, contain additives (i.e., growth and crystal morphology modifiers), suspension stabilizing additives (stabilizers), and surfactants. The precipitation can take place at a temperature from 1 to about 95 degrees C, preferably 4 to 30 degrees C. In preferred embodiments, the temperature of the contents of the reaction vessel is controlled to within $\pm 2.0$ degrees C, more preferably $\pm 0.5$ degrees C.

In accordance with the present invention, the rate of reagents addition is determined from the stoichiometry of the underlying chemical reaction(s). As complete precipitation of Mn cation as determined by equilibria is desirable; therefore, the other reagent is added in a slight to moderate excess.

In the present invention, the size, size distribution, morphology, and the degree of agglomeration of precipitated manganese particles is manipulated by the use of specific addition rates, initial volume of the host solution, and addition of certain additives, such as electrolytes, stabilizers, and surfactants to the host solution and/or to either or both reagents.

Furthermore, the duration of the reagent addition is determined by the desired final solid content and the volume of the suspension, and the addition rate applied. The addition rate can be maintained by any means of volumetric or gravimetric flow rate control, such as a manual or automatic (including computer-driven) pump speed or displacement control or by control of the hydrostatic pressure of the reagents.

The present invention is still further directed to a method of diagnosis comprising administering to a mammal a contrast effective amount of particles of a substantially insoluble manganese compound suspended or dispersed in a physiologically tolerable carrier and generating an NMR image of said mammal.

A contrast effective amount of particles is that amount necessary to provide tissue visualization with magnetic resonance imaging. Means for determining a contrast effective amount in a particular subject will depend, as is well known in the art, on the nature of the magnetically active material used, the mass of the subject being imaged, the sensitivity of the magnetic resonance imaging system and the like.

After administration of these particles, the subject mammal is maintained for a time period sufficient for the administered particles to be distributed throughout the subject and enter the tissues of the mammal. Typically, a sufficient time period is from about 5 minutes to about 8 hours and, preferably from about 10 minutes to about 90 minutes. The residue of the particles is visualized by imaging that tissue with a magnetic resonance imaging system.

The present invention includes the particles described above formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The compositions can be administered to humans and animals either orally, rectally, parenterally (intravenous, intramuscular or subcutaneous), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include physiological salts, dextran, and isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

Actual dosage levels of active ingredients in the compositions of the present invention may be varied so as to obtain an amount of active ingredient that is effective to obtain a desired diagnostic response for a particular composition and method of administration. The selected dosage level therefore depends upon the desired diagnostic effect, on the route of administration, on the desired duration of contrast and other factors. Dosages up to about 5 millimoles per kilogram of body weight are believed to be useful.

The following examples further illustrate the invention and are not to be construed as limiting of the specification and claims in any way.

Example 1

Manganese Carbonate 50 g of water, 100 mg of anhydrous citric acid, and 400 mg of Pluronic F-68 NF surfactant (altogether=-host solution) were added to a 100 ml beaker, mixed with a magnetic bar, placed in a 40° C. water bath to facilitate dissolution, and subsequently cooled to the room temperature. To the host solution was added a 1.0-M solution of $MnCl_2$(=manganese source) at a controlled rate of 4.0 mL/min. Simultaneously, a 1.02-M solution of $Na_2CO_3$ (=carbonate source) was added thereto at a controlled rate of 4.8 mL/min. Each addition was maintained for 1.0 minute. The final pH was adjusted to pH=7.2–7.7. The resultant suspension contained a uniform, spherilitic crystalline precipitate of the mean grain diameter being 400 nm, as measured by a scanning electron microscopy (=SEM). The free manganese concentration of this suspension, measured by an inductively coupled plasma atomic emission spectroscopy (=ICP-AES), was less than 90 μg/mL. Variations of the above formula, each resulting in similar or different: suspension density, morphology of precipitate, mean size, size distribution, the concentration of free manganese, and the degree of particle agglomeration:

The manganese source could be any other water-soluble salt of manganese, such as Mn $(NO_3)_2$, $MnSO_4$, etc, and may contain a nontoxic ionic additive, e.g. 0.5 g of NH4Cl and/or 0.68 g of Al2(SO4)3.18H2O, to prevent agglomeration.

The carbonate source may be any other water-soluble carbonate, such as ammonium carbonate, potassium carbonate, etc.

The host solution may be: (a) water, (b) water and citric acid, (c) water and sodium citrate, (d) as in Example 1, except that the concentration of Pluronic surfactant may vary from 0–5 wt.%, (e) as in Example 1, except that Pluronic surfactant is replaced by any or a mixture of nontoxic surfactant or stabilizer, such as: DMPG, Tetronic 908, Tween 20, Tween 80, Pluronic F-108, Tyloxapol, Henkel APG 325cs, polyvinyl alcohol, PVP k-15, ascorbic acid, etc., whose concentration may vary from 0–5 wt %, (f) any variation given above and an ionic additive, such as NH4Cl Al2(SO4)3.18H2O, in the amount of 0–1 wt %.

The surfactants, stabilizers, and/or ionic additives listed above, and/or citric acid, and/or sodium citrate, may be added to one, two or all three of the following: the manganese source, the carbonate source and the host solution.

The concentration of reagents, and/or the flow rates, and/or the time of addition may be different than given in Example 1.

Example 2

Manganese (II) Phosphate 50 g of water, 100 mg of anhydrous citric acid, and 400 mg of Pluronic F68 NF surfactant were added to a 100-mL beaker, mixed with a magnetic bar, placed in a 40° C. water bath to facilitate dissolution, and subsequently cooled to the room temperature. To this host solution was added a 1.0-M solution of MnCl2 at a controlled rate of 4.0 mL/min. Simultaneously, a 0.68-M solution of Na3PO4 was added thereto at a controlled rate of 6.0 mL/min. Each addition was maintained for 1.0 minute. The final pH was adjusted to pH=7.2–7.7. The resultant suspension contained a crystalline precipitate of the mean grain size being 150 nm, as measured by SEM. The suspension's free manganese concentration measured by ICP-AES, was less than 10 $\mu$g/mL. Variations of the above formula, each resulting in similar or different: suspension density, morphology of precipitate, mean size, size distribution, the concentration of free manganese, and the degree of particle agglomeration:

The manganese source could be any other water-soluble salt of manganese, such as Mn(NO3)2, MnSO4, MnF2, manganese acetate, etc., and may contain a nontoxic ionic additive, e.g. 0.5 g of NH4Cl and/or 0.68 g of Al2(SO4)3.18H2O, to prevent agglomeration.

The phosphate source may be any other water-soluble phosphate such as sodium phosphate, dibasic; sodium phosphate, monobasic; potassium phosphate, dibasic; potassium phosphate, monobasic; ammonium phosphate, dibasic; ammonium phosphate, monobasic; etc.

The host solution may be: (a) water, (b) water and citric acid, (c) water and sodium citrate, (d) as in Example 2, except that the concentration of Pluronic surfactant may vary from 0–5 wt %; (e) as in Example 2, except that Pluronic surfactant is replaced by any or a mixture of other nontoxic surfactants or stabilizers, such as: DMPG, Tetronic 908, Tween 20, Tween 80, Pluronic F-108, Tyloxapol, Henkel APG 325cs, polyvinyl alcohol, PVP k-15, etc., whose concentration may vary from 0–5 wt %, (f) any variation given above and an ionic additive, such as NH4Cl, Al2(SO4)3.18H2O, in the amount of 0–1 wt %.

The surfactants, stabilizers, and/or ionic additives listed above, and/or citric acid, and/or sodium citrate, may be added to one, two or all three of the following: the manganese source, the phosphate source and the host solution.

The concentration of reagents, and/or the flow rates, and/or the time of addition may be different than given in Example 2.

Example 3.

Manganese (II) 8-hydroxy quinolinate 77.50 g of 1.0-M HCl was mixed with 8.00 g of 8-quinolinol at the room temperature until dissolved. 13.40 g of a such prepared solution, 36.00 g of water, 500 mg of Tween 20, and 500 mg of Tween 80 were added to a 100-mL beaker, and mixed with a magnetic bar. To this host solution was added a 1.0-M solution of MNCl2 at a controlled rate of 4.0 mL/min. Simultaneously, a 2.0-M solution of NaOH (=base source) was added thereto at a controlled rate of 8.5 mL/min. Each addition was maintained for 1.0 minute. The resultant suspension, whose final pH was adjusted to pH=7.2–7.7 using a diluted aqueous solution of NaOH, contained a crystalline precipitate of the mean grain size being 1,500 nm, as measured by SEM. The suspension's free manganese concentration, measured by ICP-AES, was less than 2 $\mu$g/ML. Variations of the above formula, each resulting in similar or different: suspension density, morphology of precipitate, mean size, size distribution, the concentration of free manganese, and the degree of particle agglomeration:

The manganese source could be any other water-soluble salt of manganese, such as Mn(No3)2, MnSO4, manganese acetate, manganese fluoride, etc., and may contain a nontoxic ionic additive, e.g. 0.5 g of NH4Cl and/or 0.68 g of Al2(SO4)3.18H2O, to prevent agglomeration.

8-quinolinol may be dissolved in a base rather than in an acid. The examples of such a base include NaOH or KOH. Then, an addition of an acid rather than of a base accompanies the addition of the manganese source. Examples of such an acid include HCl, HNO3, H2SO4, etc.

The mixture of the Tween surfactants in Example 3, may be replaced by any or a mixture of the following nontoxic surfactants or stabilizers: DMPG, Tetronic 908, Tween 20, Tween 80, Pluronic F-108, Tyloxapol, Henkel APG 325cs, polyvinyl alcohol, PVP k-15, etc., whose concentration may vary from 0–5%. The host solution may contain an ionic additive, such as NH4Cl Al2(SO4)3.18H2O, in the amount of 0–1 wt %.

The host solution may contain citric acid and/or sodium citrate.

The surfactants, stabilizers, and/or ionic additives listed above, and/or citric acid, and/or sodium citrate, may be added to one, two or all three of the following: the manganese source, the base/acid source and the host solution.

The concentration of reagents, and/or the flow rates, and/or the time of addition may be different than given in Example 3.

Example 4

Several of the formulations from the above examples 1–3 were examined for their size, zeta potential (ZP), plasma stability, and whether the particular compositions could be autoclaved. The results of these studies are shown in Table 1.

TABLE 1

| Surfactant | Size (PCS)* | ZP (mV) | Plasma Stability | Autoclavable |
|---|---|---|---|---|
| F68 | 1.8 μm | −16.2 | Fine | Yes |
| DS20HDA | 822 nm | −16.4 | Fine | |
| T1508 | 1.6 μm | −15.7 | | |
| TWEEN20 | 2.2 μm | −13.9 | | |
| OMLF108 | 1.4 μm | −14.4 | | |
| DOSS | 639 nm | −15.8 | Fine | Yes |
| SA90HAQ | 829 nm | −17.4 | | |
| DMPG | 613 nm | −24.3 | Fine | |

*Photon correlation spectroscopy

Example 5

Figure 2:
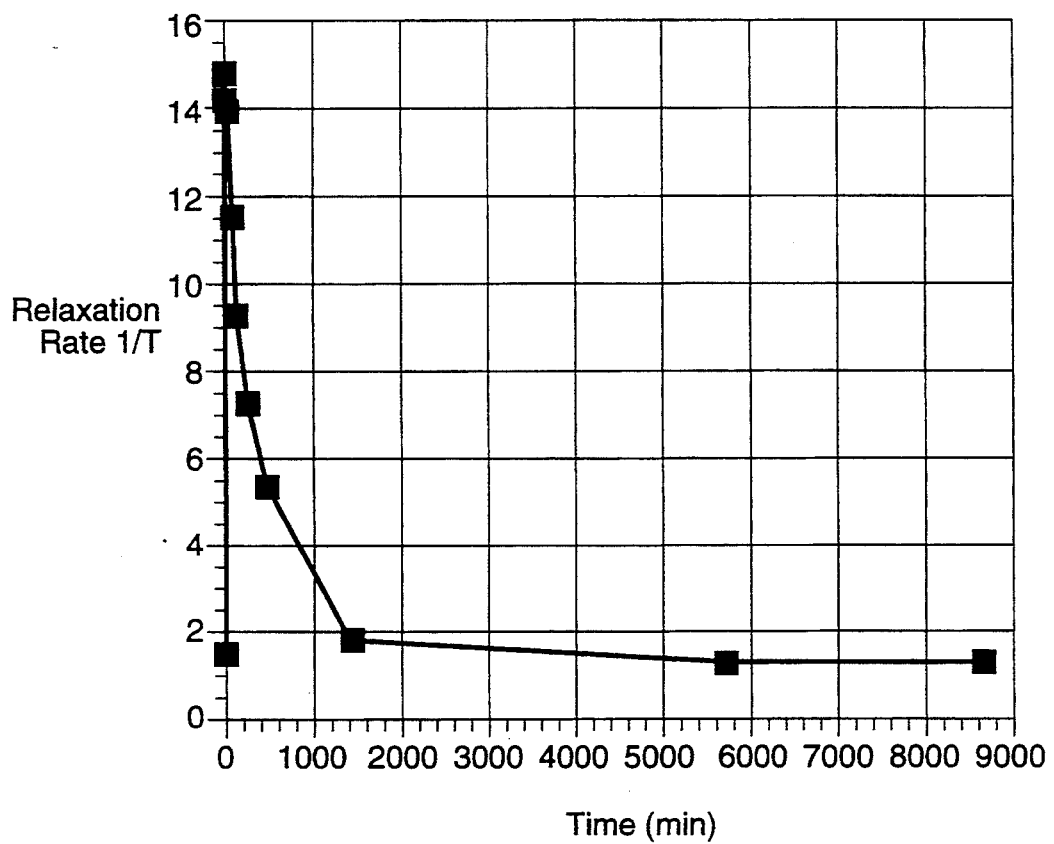
FIG. 2 shows the change in relaxivity of the tissue with time after injection of the insoluble manganese particles of the present invention.

The hepatic clearing of manganese particles made in accordance to the processes of the present invention was tested. Animals were injected via the tail vein with 50 μmoles per kilogram of body weight with manganese particles. At various times thereafter, the animals were euthanized and the livers of the animals were excised. Livers were frozen until assay, and then homogenized prior to the assay. The results of these experiments are shown in FIGS. 1 and 2. In FIG. 1, the time course of hepatic clearance was studied from 0 to 500 minutes after administration of the manganese particles. In FIG. 2, the time course of hepatic clearance was studied from 0 to 9000 minutes after administration.

Example 6

Figure 3:
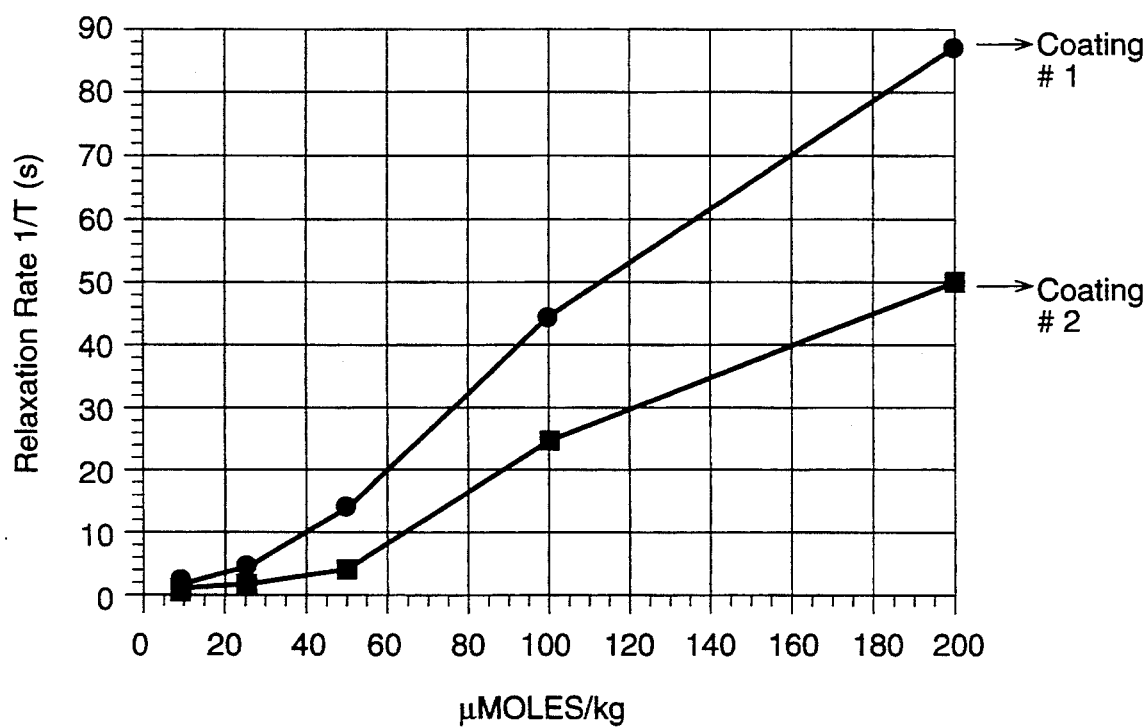
FIG. 3 shows the effect of surfactant coatings on the relaxation rate of the liver following injection into the tail veins of test animals of various dosages of insoluble manganese particles of the present invention.

The effects of surfactant coatings on the relaxation rate of the liver was studied using manganese particles prepared in accordance with the processes of the present invention. Animals were injected via the tail vein with the particles at various doses ranging from 5μ moles per kilogram of body weight to 200μ moles per kilogram of body weight. After 30 minutes, the animals were euthanized, and the livers were excised. Livers were homogenized 1:1 (w/v) with saline, and then the relaxation rate of the homogenate was determined. The results are shown in FIG. 3.

Example 7

The compositions of the invention produced impressive images of the liver. A formulation of manganese carbonate particles stabilized with DMPG provided optimal imaging 5 to 30 minutes post injection. A formulation of manganese carbonate particles stabilized with F68 provided optimal imaging 30 minutes to 2 hours post injection.

The foregoing specification, including the specific embodiments and examples is intended to be illustrative of the present invention and is not to be taken as limiting. Numerous other variations and modifications can be effected without departing from the true spirit and scope of the present invention.

We claim:

1. A method of diagnosis of an organ rich in mitochondria of a mammal comprising administering to the mammal a contrast effective amount of particles of a substantially insoluble manganese compound in the form of a manganese salt wherein said particles do not significantly alter $T_1$ or $T_2$ suspended or dispersed in a physiologically tolerable carrier and generating an NMR image of said mammal.

2. The method of claim 1 wherein said organ rich in mitochondria is the liver, kidney, pancreas or biliary network.

3. The method of claim 1 wherein said particles have a particle size of less than about 10 microns.

4. The method of claim 1 wherein said particles have a particle size of less than 5 microns.

5. The method of claim 1 wherein said manganese compound is selected from the group consisting of manganese phosphate and manganese carbonate.

6. The method of claim 1 wherein said carrier further comprises a surfactant.

7. The method of claim 6 wherein said surfactant is dimyristoylphosphatidylglycerol.

* * * * *